United States Patent
Joseph

(10) Patent No.: US 9,486,187 B2
(45) Date of Patent: Nov. 8, 2016

(54) WIND UP DEPLOYMENT MECHANISMS FOR SURGICAL INSTRUMENTS

(71) Applicant: COVIDIEN LP, Mansfield, MA (US)

(72) Inventor: Daniel A. Joseph, Golden, CO (US)

(73) Assignee: COVIDIEN LP, Mansfield, MA (US)

( * ) Notice: Subject to any disclaimer, the term of this patent is extended or adjusted under 35 U.S.C. 154(b) by 174 days.

(21) Appl. No.: 14/335,126

(22) Filed: Jul. 18, 2014

(65) Prior Publication Data
US 2015/0082922 A1    Mar. 26, 2015

Related U.S. Application Data

(60) Provisional application No. 61/882,766, filed on Sep. 26, 2013.

(51) Int. Cl.
| | |
|---|---|
| F16H 25/08 | (2006.01) |
| F16H 25/16 | (2006.01) |
| A61B 17/00 | (2006.01) |
| A61B 17/29 | (2006.01) |
| A61B 17/068 | (2006.01) |
| A61B 17/072 | (2006.01) |

(52) U.S. Cl.
CPC ............ *A61B 17/00* (2013.01); *A61B 17/29* (2013.01); *A61B 17/2909* (2013.01); *A61B 17/068* (2013.01); *A61B 2017/0046* (2013.01); *A61B 2017/00398* (2013.01); *A61B 2017/00407* (2013.01); *A61B 2017/00411* (2013.01); *A61B 2017/07285* (2013.01); *A61B 2017/2912* (2013.01); *A61B 2017/2946* (2013.01); *A61B 2090/0807* (2016.02); *Y10T 74/18288* (2015.01)

(58) Field of Classification Search
CPC ............ A61B 2017/2913; A61B 2017/2915; A61B 2017/0411; A61B 2017/2946; A61B 2017/928; A61B 2017/925; A61B 2018/00196; A61B 17/2909; A61B 2017/00407; A61B 5/15117
See application file for complete search history.

(56) References Cited

U.S. PATENT DOCUMENTS

| | | | |
|---|---|---|---|
| 4,876,794 A * | 10/1989 | Myers | B25B 7/12 30/247 |
| 5,554,154 A | 9/1996 | Rosenberg | |
| 7,763,042 B2 * | 7/2010 | Iio | A61B 5/1411 600/583 |
| 8,360,061 B2 | 1/2013 | Brown et al. | |
| 8,870,912 B2 * | 10/2014 | Brisson | A61B 17/295 606/208 |
| 2005/0131441 A1 * | 6/2005 | Iio | A61B 5/1411 606/182 |
| 2009/0118641 A1 | 5/2009 | Van Dam et al. | |
| 2010/0152759 A1 * | 6/2010 | List | A61B 5/1411 606/172 |
| 2010/0168618 A1 * | 7/2010 | List | A61B 5/1411 600/583 |
| 2012/0172752 A1 | 7/2012 | Ranpura et al. | |
| 2013/0096459 A1 | 4/2013 | Vetter | |

* cited by examiner

*Primary Examiner* — William Kelleher
*Assistant Examiner* — Jake Cook

(57) ABSTRACT

A surgical instrument includes a handle assembly having an actuating rod extending therefrom, a rotating member, a release member, and a stop, the actuating rod translatable along a longitudinal axis defined therethrough. The rotating member is disposed within the handle assembly and is configured to operably engage the actuating rod via a cam and link arrangement. The release member includes a first catch configured to lock the rotating member against the force of an energy storage device in a first condition and release the rotating member to rotate in an opposite direction with the force of the energy storage device in a second condition. The stop is disposed on a peripheral edge of the rotating member and is configured to operably engage the first catch when the release member is disposed in the first condition to limit the rotational movement of the rotating member.

21 Claims, 8 Drawing Sheets

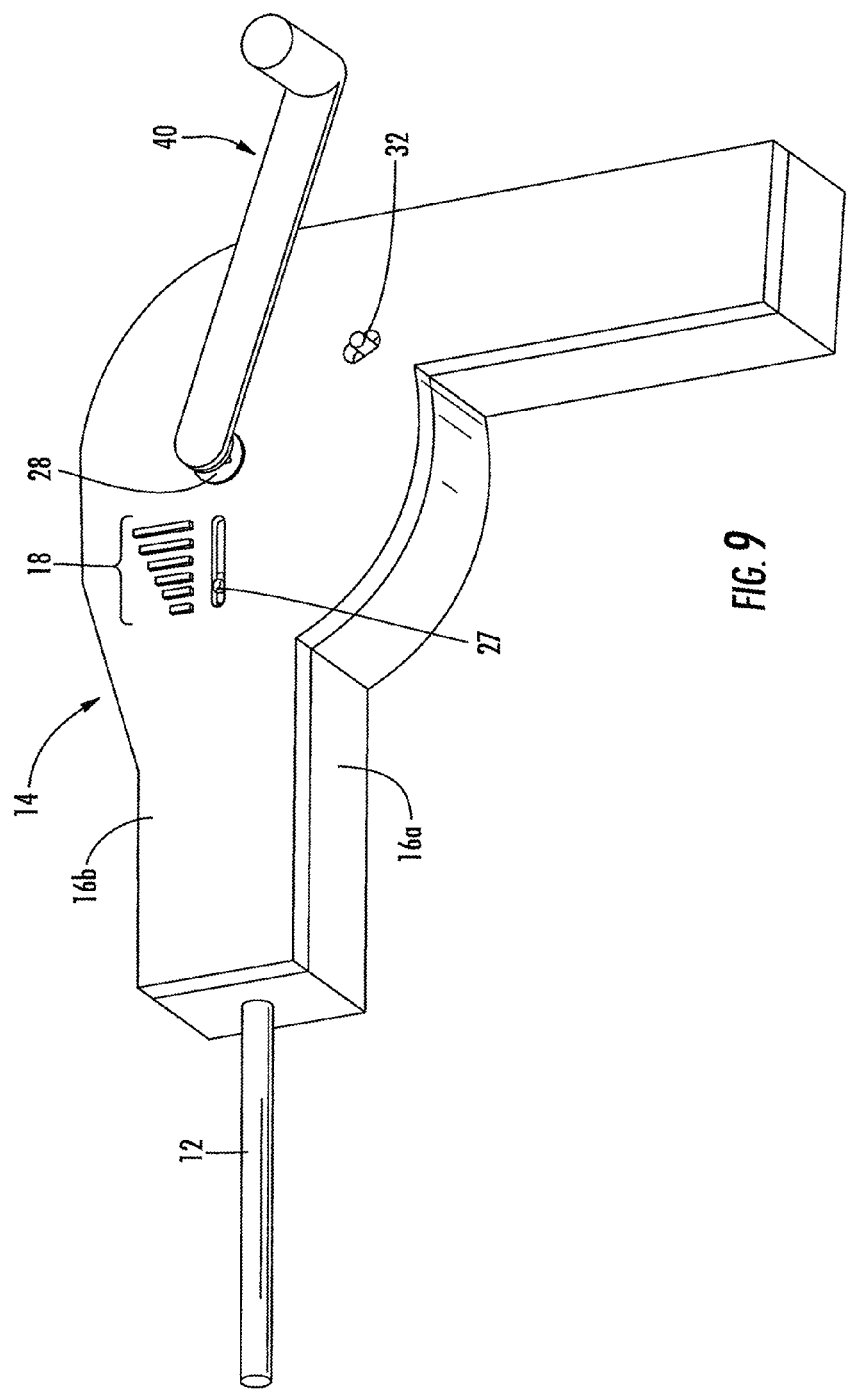

WIND UP DEPLOYMENT MECHANISMS FOR SURGICAL INSTRUMENTS

CROSS REFERENCE TO RELATED APPLICATION

The present application claims the benefit of and priority to U.S. Provisional Application Ser. No. 61/882,766, filed on Sep. 26, 2013, the entire contents of which are incorporated herein by reference.

BACKGROUND

1. Technical Field

The present disclosure relates to surgical instruments and, more specifically, to deployment mechanisms configured to deploy, e.g., actuate, one or more components of a surgical instrument.

2. Discussion of Related Art

Many surgical instruments include one or more movable handles, levers, actuators, triggers, etc. for actuating and/or manipulating one or more functional components of the surgical instrument. For example, a surgical forceps may include a movable handle that is selectively compressible relative to a stationary handle for moving opposing first and second jaw members between spaced-apart and approximated positions for grasping tissue therebetween. Such a forceps may further include a trigger configured to allow selective deployment of a knife between the jaw members to cut tissue grasped therebetween.

As can be appreciated, as additional functional components are added to the surgical instrument, additional deployment structures capable of actuating more than one component are required. However, multiple deployment structures and/or combined deployment structures may be limited by functional constraints of the components, e.g., a combined deployment structure may impart additional force requirements for deploying one or more of the components coupled thereto.

SUMMARY

Accordingly, there is an existing need for instruments that simplify the actuation and/or reduce the force required to actuate the components of mechanical instruments.

In an aspect of the present disclosure, a surgical instrument includes a handle assembly, a rotating member, a release member, and a stop. The handle assembly includes an actuating rod extending therefrom. The actuating rod defines a longitudinal axis and is configured to translate along the longitudinal axis. The rotating member is disposed within the handle assembly and is operably engaged to the actuating rod via a cam and link arraignment. The cam and link arraignment is configured to convert the rotational movement of the rotating member into longitudinal translation of the actuating rod. The rotating member is movable in a first direction to bias an energy storage device (e.g., a spring).

The release member includes a first catch configured to lock the rotating member against the force of the energy storage device in a first condition and upon actuation thereof is configured to release the rotating member to rotate in an opposite direction with the force of the energy storage device in a second condition. The stop is disposed on a peripheral edge of the rotating member and is configured to engage the first catch when the release member is disposed in the first condition. The stop is configured to limit the rotational movement of the rotating member as the rotating member moves in the opposite direction. In one embodiment, the energy storage device may be a torsion spring.

In aspects of the present disclosure, the surgical instrument includes a release switch configured to move the release member between the first and second conditions. In some embodiments, the surgical instrument includes a release biasing member configured to urge the release member towards the first condition to limit rotational movement of the rotating member.

In aspects of the present disclosure, the handle assembly may include a window and the energy storage device may include a power indicator. The power indicator may be viewable through the window defined in the handle assembly. The handle assembly may also include an energy gauge proximate the window which cooperates with the power indicator to display an amount of energy stored by (or remaining in) the energy storage device.

In aspects of the present disclosure, the release member may include a second catch that is selectively engagable with the stop and that is configured to toggle with the first catch to limit the rotational movement of the rotating member.

In aspects of the present disclosure, the rotating member includes first and second stops equally spaced about the peripheral edge of the rotating member relative to each other. In embodiments, the first stop may be positioned on the peripheral edge of the rotating member such that when the first stop engages the first catch the actuating rod is disposed in an extended position. The second stop may be positioned on the peripheral edge of the rotating member such that when the second stop engages the first catch the actuating rod is disposed in a retracted position.

In aspects of the present disclosure, a rotatable shaft is operatively associated with the energy storage device. The rotatable shaft is selectively movable to rotate the rotating member against the bias of the energy storage device. The instrument may include a crank configured to engage the rotatable shaft to manually rotate the rotating member to bias the energy storage device.

In aspects of the present disclosure, the stop may include a trailing surface having a ramp configured to urge the first catch of the release member away from the peripheral edge of the rotating member when the rotating member is rotated in the first direction. The trailing surface may be configured to facilitate the rotation of the rotating member against the bias of the energy storage device.

According to aspects of the present disclosure, a method for actuating a surgical instrument includes biasing an energy storage device of a surgical instrument in a first direction, locking the rotating member against the force of the energy storage device, and translating the actuating rod along a longitudinal axis of the surgical instrument. The surgical instrument may be any of the surgical instruments described herein. Locking the rotating member against the force of the energy storage device includes engaging the one or more stops with the first catch of the release member. Translating the actuating rod along the longitudinal axis includes releasing at least a portion of the energy from the energy device.

In some embodiments, translating the actuating rod includes converting the rotational movement of the rotating member into longitudinal translation of the actuation rod via a cam and link arrangement that is operatively engaged with the rotating member and the actuating rod. The method may include determining the amount of energy stored within the energy storage device by viewing a power indicator through a window defined by the handle assembly. Biasing the energy storage device in the first direction includes the one or more stops urging the first catch of the release member away from the rotating member as the rotating member is rotated in the first direction.

In certain embodiments, translating the actuating rod includes releasing the rotating member by disengaging the first catch of the release member from the one or more stops to permit the rotating member to rotate in a second direction opposite the first direction with the force of the energy storage device. The method may include limiting the rotational movement of the rotating member as the rotating member moves in the second direction with a second catch of the release member. Disengaging the first catch of the release member includes toggling a release switch operatively associated with the release member.

BRIEF DESCRIPTION OF THE DRAWINGS

Various aspects of the present disclosure are described hereinbelow with reference to the drawings, wherein:

FIG. 9 is a front perspective view of the instrument shown in FIG. 1 engaged with a manual crank.

DETAILED DESCRIPTION

Figure 1:
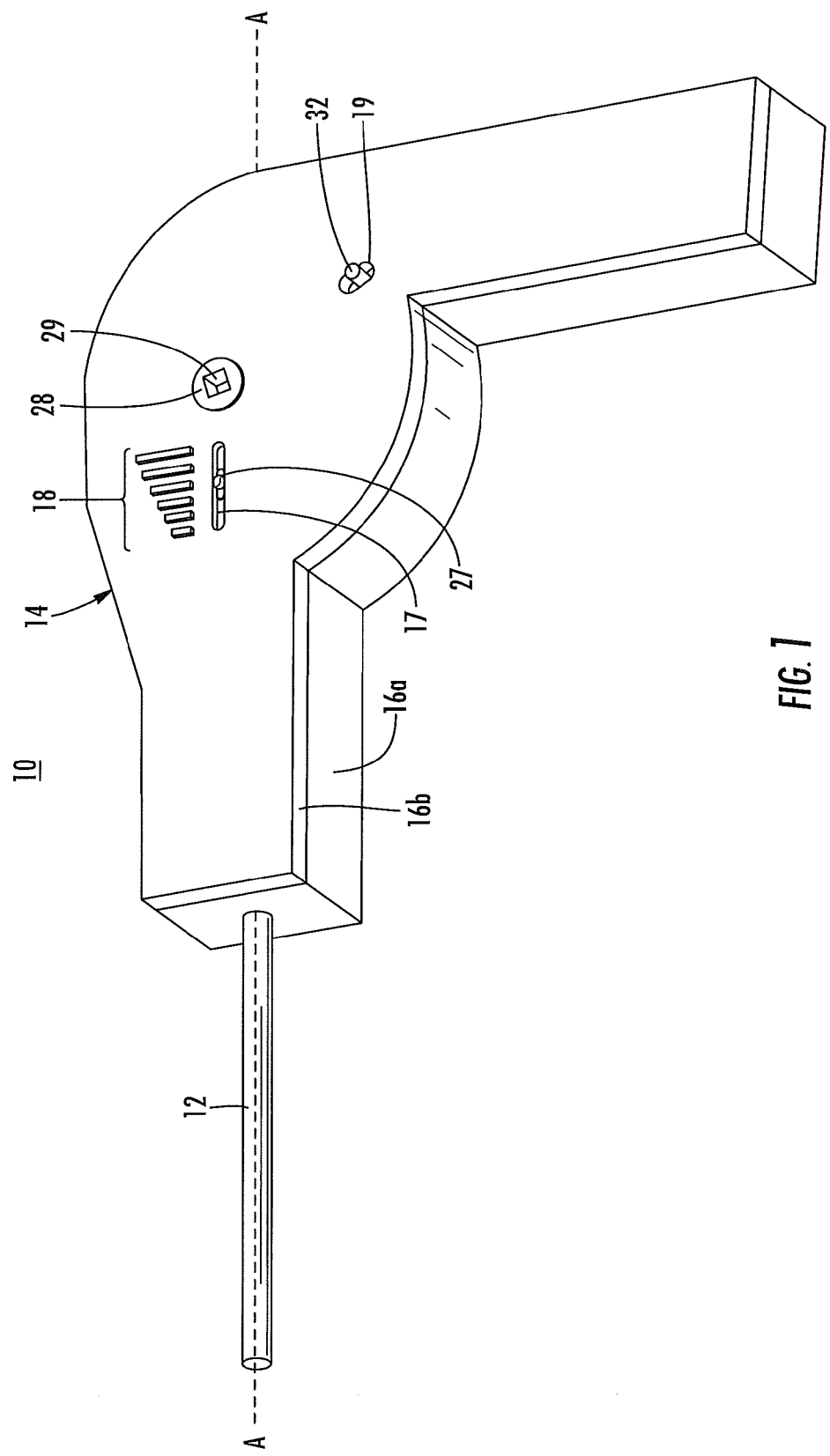
FIG. 1 is a front perspective view of an example embodiment of a surgical instrument provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is further from the clinician.

Figure 2:
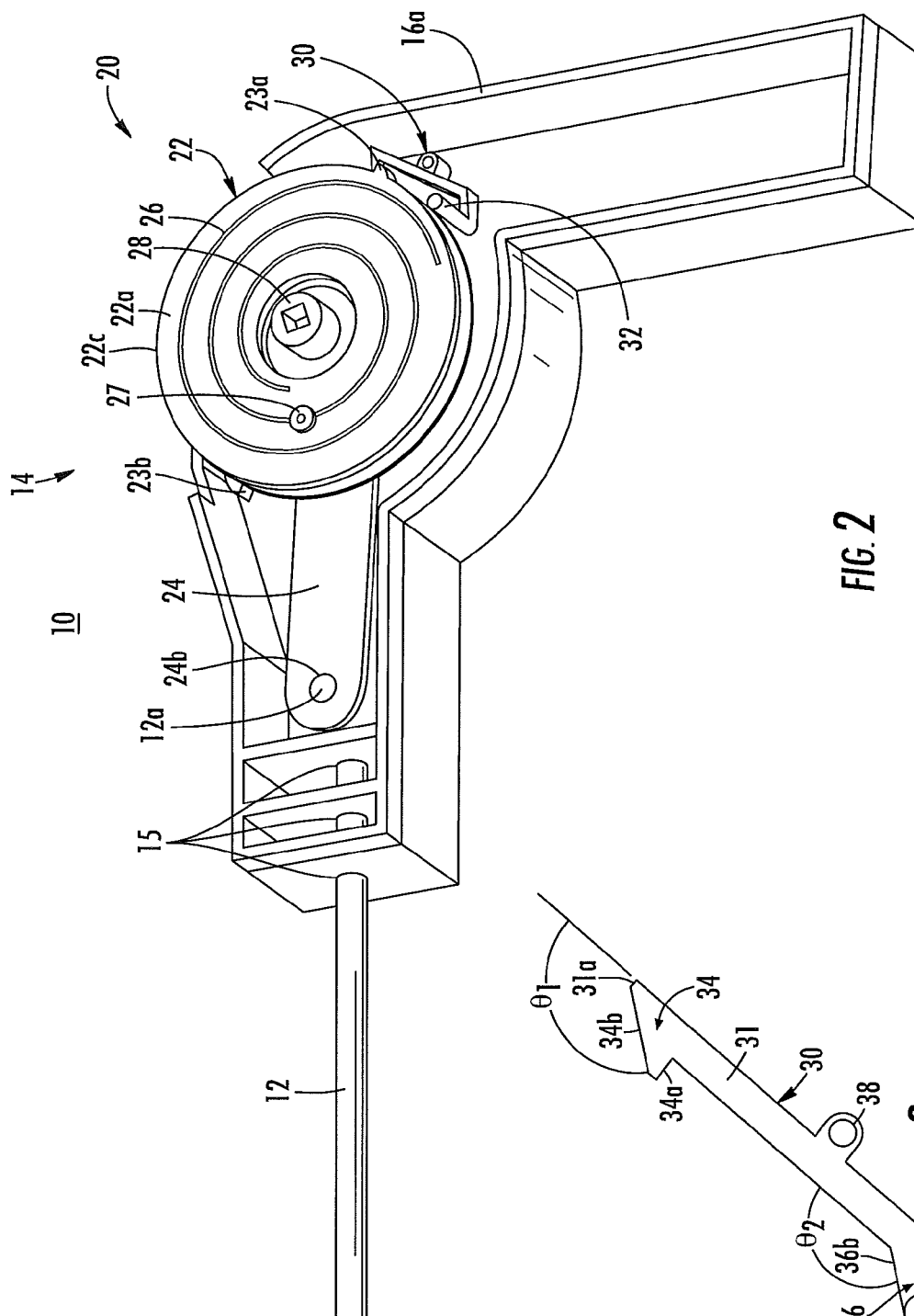
FIG. 2 is a front perspective view with a portion of an outer body shell removed showing the internal components of the instrument shown in FIG. 1.

Referring now to FIGS. 1 and 2, a surgical instrument 10 is provided in accordance with the present disclosure incorporating an actuating rod 12, a handle assembly 14, and a deployment mechanism 20. Actuating rod 12 defines a longitudinal axis "A-A" and translates along the longitudinal axis "A-A." Actuating rod 12 can be coupled to a source of electrosurgical energy and configured to deliver the electrosurgical energy to tissue. Electrosurgical energy may be microwave energy, RF energy, light energy, ultrasonic energy, optical energy, thermal energy, etc. Actuating rod 12 can include a tool assembly or tip (not shown), e.g., a hook, a blade, or jaws, positioned at the distal end thereof.

Handle assembly 14 includes body shells 16a, 16b. Handle assembly 14 includes openings 15 defined in body shell 16a. Openings 15 are longitudinally aligned to limit movement of actuating rod 12 to translation along and rotation about longitudinal axis "A-A." Body shells 16a, 16b may be joined together by screwing, ultrasonic welding, gluing, or any other suitable methods of combining parts.

Body shell 16b includes a window 17, an energy gauge 18, and a slot 19 defined therein, the details of which are described below.

Figure 4:
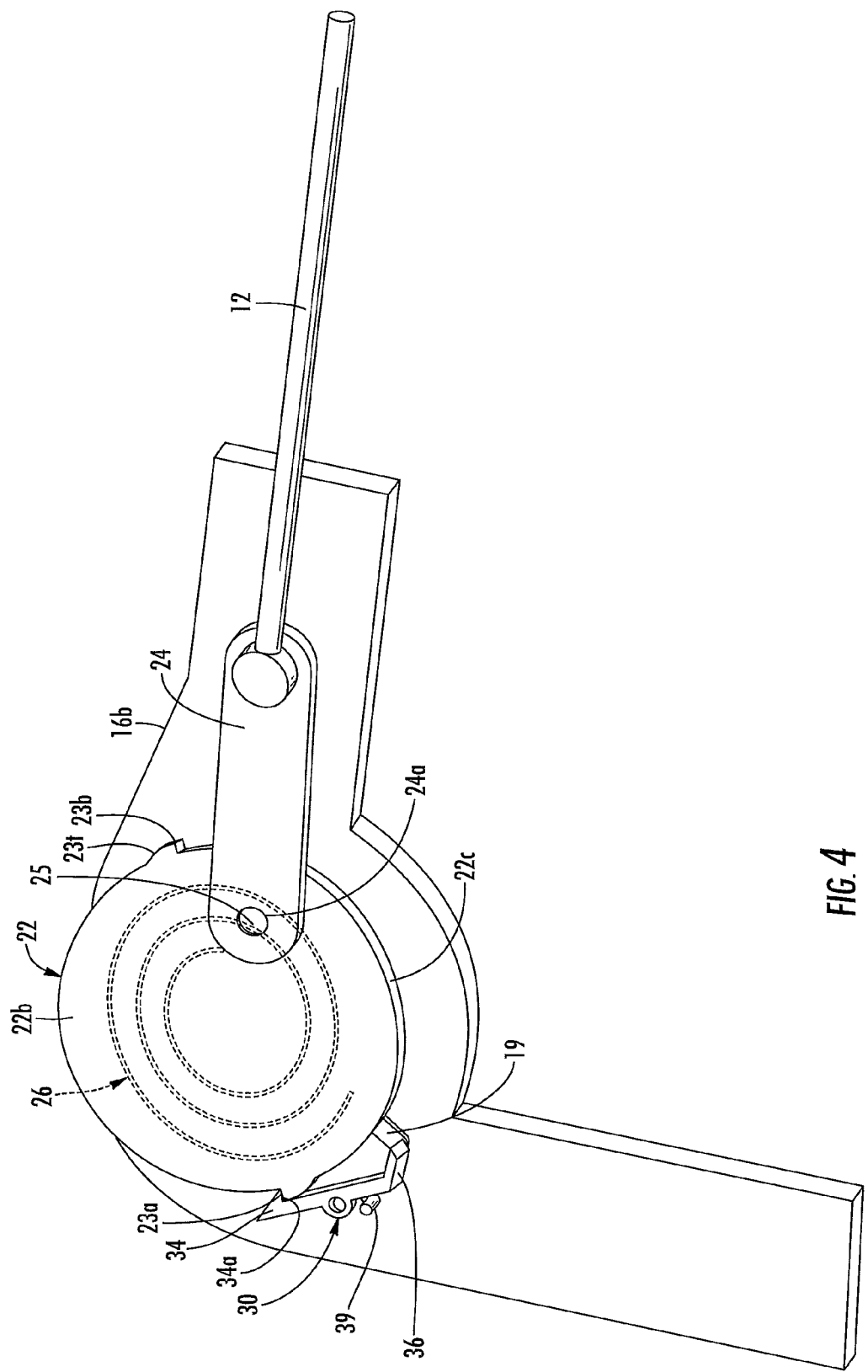
FIGS. 4-8 are a progression of rear perspective views illustrating the operation of the internal components of the instrument shown in FIG. 1.

Referring to FIGS. 2 and 4, deployment mechanism 20 is positioned between body shells 16a, 16b and includes a rotating member 22, a connecting link 24, an energy storage device 26 (e.g., a torsion spring), and a release member 30. As shown, rotating member 22 is circular or disc-shaped; however, it is contemplated that rotating member 22 may be any shape that is rotatable between body shells 16a, 16b, e.g., rectangular, triangular, octagonal, etc. Rotating member 22 includes a front or first surface 22a, a back or second surface 22b, and an outer circumference or peripheral edge 22c. Rotating member 22 includes stops 23a, 23b defined on a peripheral edge 22c thereof that are configured to selectively engage release member 30, as described in more detail below. Rotating member 22 may include any number of stops depending upon a particular purpose or to achieve a particular result. For example, one stop 23a may be utilized to allow the rotating member 22 to complete a full cycle which includes the deployment and retraction of the actuating rod 12 in a stab-like manner for spot coagulation. Two or more stops 23a, 23b, etc. may be utilized to stop the rotating member 22 and actuating rod 12 at more than one deployed or retracted position. In embodiments with two or more stops, the stops may be equally spaced or unevenly spaced about peripheral edge 22c of rotating member 22. In some embodiments, stops 23a, 23b are integrally formed on peripheral edge 22c of rotating member 22. In some embodiments, stops 23a, 23b protrude from first surface 22a of rotating member 22 near peripheral edge 22c thereof. Second surface 22b includes a cam 25 near peripheral edge 22c of rotating member 22. Cam 25 is designed to engage connecting link 24 to translate (e.g., deploy and retract) actuating rod 12 along longitudinal axis "A-A" as cam 25 cooperates with the rotation of rotating member 22.

Energy storage device 26 is operatively associated with rotating member 22. Energy storage device 26 is configured to store energy such that when rotating member 22 is rotated in a first direction (e.g., counter-clockwise as shown in FIG. 4), energy storage device 26 stores energy. Once rotating member 22 is released, via release member 30, energy is released from energy storage device 26 and rotating member 22 is forced to rotate in a second opposite direction (e.g., clockwise).

Energy storage device 26 may include a power indicator 27 positioned on a portion of energy storage device 26. Indicator 27 is viewable through window 17 (FIG. 1) defined in body shell 16b to provide a visual indication of the amount of energy stored by energy storage device 26 or left in energy storage device 26. Energy gauge 18 may include visual indicia of predefined amounts of energy stored (i.e., potential energy) within energy storage device 26. The predefined amount of energy can represent one of a number of rotations of rotating member 22, an amount of time rotating member 22 will rotate, or a percentage of energy stored relative to a maximum amount of stored energy. Energy storage device 26 may include one or more over wind protection features (not shown).

Figure 3:
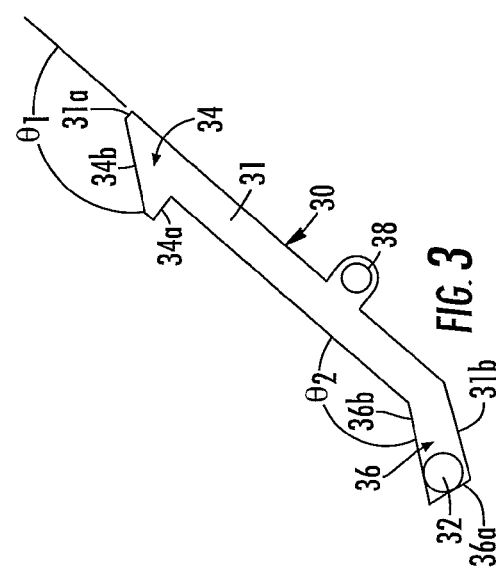
FIG. 3 is a side view of a release mechanism shown in FIG. 2.

Referring to FIG. 3, release member 30 is configured to selectively engage stops 23a, 23b (FIG. 2) of rotating member 22. This selective engagement permits deployment mechanism 20 to store and release energy from energy storage device 26, as described in detail below. Release member 30 includes a back span 31, a release switch 32, a first catch 34, a second catch 36, and a pivot member 38. Back span 31 has leading and trailing ends 31a, 31b. Back span 31 extends between first and second catches 34, 36. Release switch 32 protrudes through a slot 19 defined in body shell 16*b* (see FIG. 1) and is selectively engageable by a clinician. Release switch 32 can be positioned proximate or on trailing end 31*b* of back span 31. First catch 34 has a first leading surface 34*a* and a first trailing surface 34*b*. Second catch 36 has a second leading surface 36*a* and a second trailing surface 36*b*. Leading surfaces 34*a*, 36*a* of first and second catches 34, 36 are substantially orthogonal to back span 31 and provide a point of contact with peripheral edge 22*c* of rotating member 22. Trailing surfaces 34*b*, 36*b* of first and second catches 34, 36 define angles $\theta_1$, $\theta_2$ with back span 31. Pivot member 38 is positioned on back span 31 to provide a pivot point for release member 30.

With reference to FIG. 4, connecting link 24 includes proximal and distal ends and is configured to convert the rotational movement of rotating member 22 into translation of the actuating rod 12 along longitudinal axis "A-A." The proximal end of connecting link 24 includes a proximal opening 24*a* defined therethrough that is configured to pivotally receive cam 25. The distal end of connecting link 24 is configured to operatively engage actuating rod 12. The distal end of connecting link 24 includes a distal opening 24*b* (see FIG. 2) that receives a pin 12*a* (see FIG. 2). Connecting link 24 engages pin 12*a* (see FIG. 2) to translate actuating rod 12 along longitudinal axis "A-A."

Deployment mechanism 20 may include additional actuation rods (not shown) each operatively coupled with an additional cam (not shown) to translate the additional actuating rods with respect to the longitudinal axis. Each additional cam can protrude a different distance from first or second surfaces 22*a*, 22*b* of rotating member 22 and can each be positioned a different distance away from peripheral edge 22*c* of rotating member 22.

Figure 5:
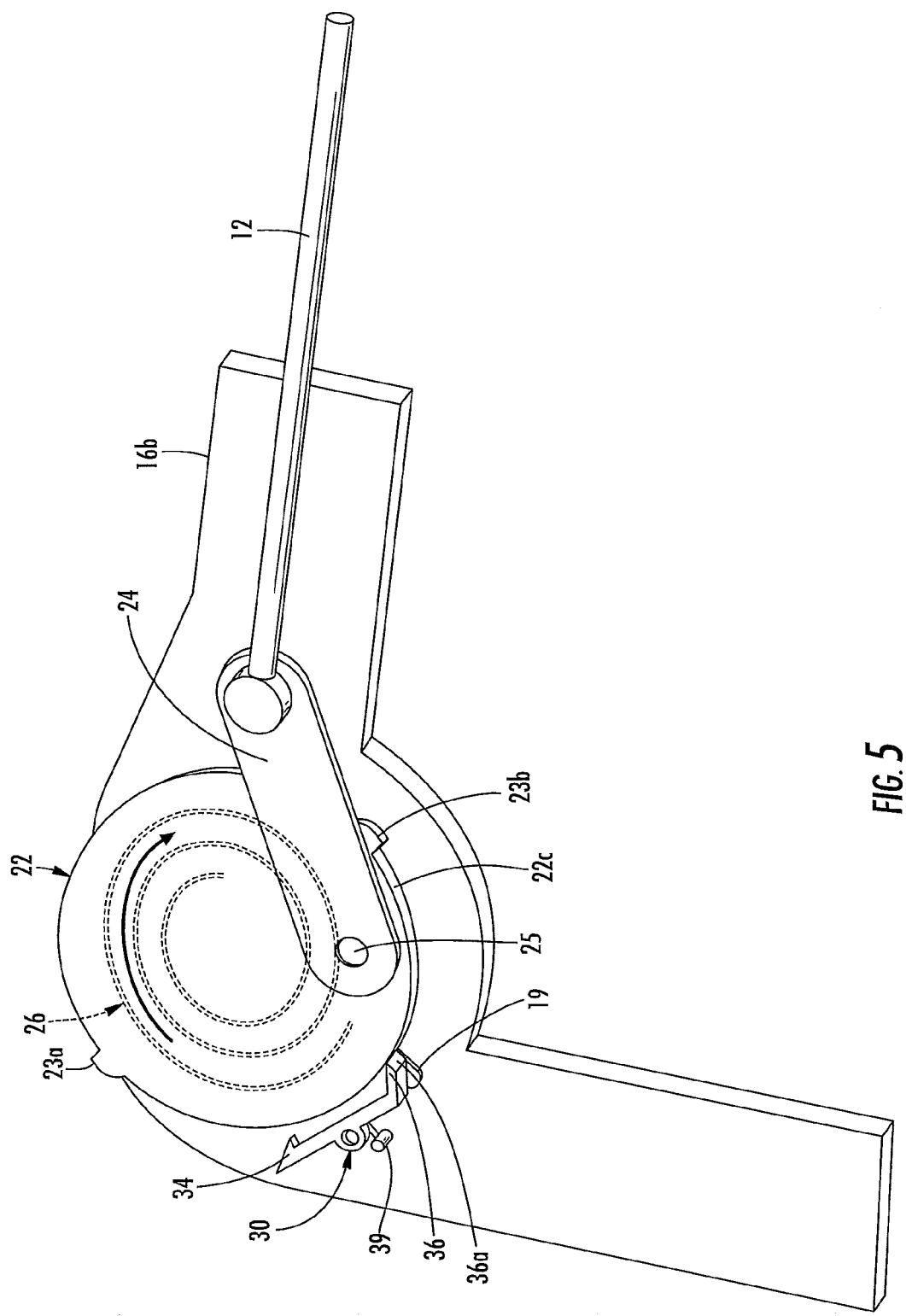

Referring to FIGS. 4 and 5, release member 30 has a first condition (FIG. 4) and a second condition (FIG. 5). In the first condition (FIG. 4), first catch 34 is proximate peripheral edge 22*c* of rotating member 22 such that leading surface 34*a* of first catch 34 is positioned to engage stops 23*a*, 23*b* and second catch 36 is spaced-apart from peripheral edge 22*c* of rotating member 22 such that stops 23*a*, 23*b* can pass between second catch 36 and peripheral edge 22*c*. In the second condition (FIG. 5), second catch 36 is positioned proximate peripheral edge 22*c* of rotating member 22 such that leading surface 36*a* of second catch 36 is positioned to engage stops 23*a*, 23*b* and first catch 34 is spaced-apart from peripheral edge 22*c* of rotating member 22 such that stops 23*a*, 23*b* can pass between second catch 36 and peripheral edge 22*c*. A biasing member 39 is included and is configured to urge release member 30 towards the first condition upon actuation of release switch 32 (see FIG. 7 below). Biasing member 39 is mounted to body shell 16*b*.

With reference to FIGS. 2 and 4-8, the translation of actuating rod 12 from an extended or deployed position (FIG. 4) to a retracted position (FIG. 8) is described and shown in detail in progressive views. As shown in FIG. 4, energy storage device 26 (shown in phantom) is rotated (via manually or automatically (not explicitly shown)) counter-clockwise to bias the rotating member 22 against the energy storage device 26 and store energy for clockwise rotation of rotating member 22. Release member 30 is disposed in the first condition such that stop 23*a* is engaged with leading surface 34*a* of first catch 34. The engagement of first catch 34 with stop 23*a* prevents energy storage device 26 from releasing the potential energy or rotating rotating member 22.

As shown in FIGS. 1 and 5, release switch 32 is moved within slot 19 to urge release member 30 against release biasing member 39 such that release member 30 transitions from the first condition to the second condition. When first catch 34 is spaced-apart from peripheral edge 22*c* of rotating member 22, the potential energy or bias of energy storage device 26 induces clockwise rotation of the rotating member 22 as shown in FIG. 5. As rotating member 22 rotates, cam 25 and link 24 cooperate with the rotation of rotating member 22 to retract actuating rod 12 along longitudinal axis "A-A."

Figure 6:
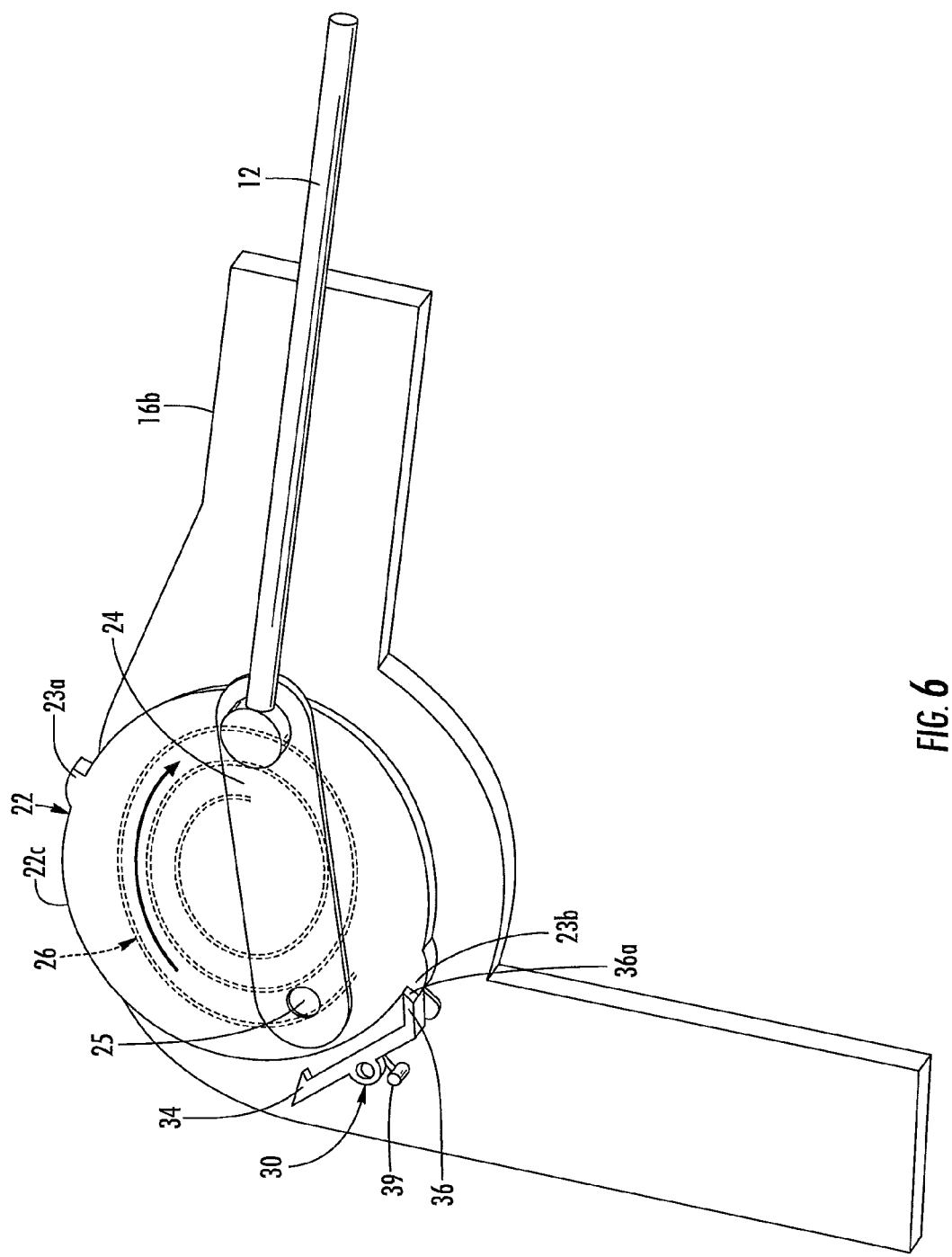

Energy storage device 26 rotates rotating member 22 until stop 23*b* engages leading surface 36*a* of second catch 36 as shown in FIG. 6. The position of release switch 32 maintains release member 30 in the second position and actuating rod 12 in a first retracted position. Second catch 36 limits the rotation of rotating member 22 and, thus, prevents further translation of actuating rod 12 until the release switch 32 is again actuated (via opposite movement of release switch 32) which disengages catch 36 from stop 23*b* and allows rotating member 22 to retract actuating rod 12 to a proximal-most position when stop 23*b* engages catch 34 (see FIG. 8). As can be appreciated, in this instance the retraction of actuation rod 12 occurs in a two-stage process and allows the clinician two retraction positions, i.e., when stop 23*b* engages second stop 36 and when stop 23*b* engages first stop 34. As explained in more detail below, the clinician will also have two extended positions by virtue of the stop 23*a*, 23*b* configuration on rotating member 22 and release member 30.

Figure 7:
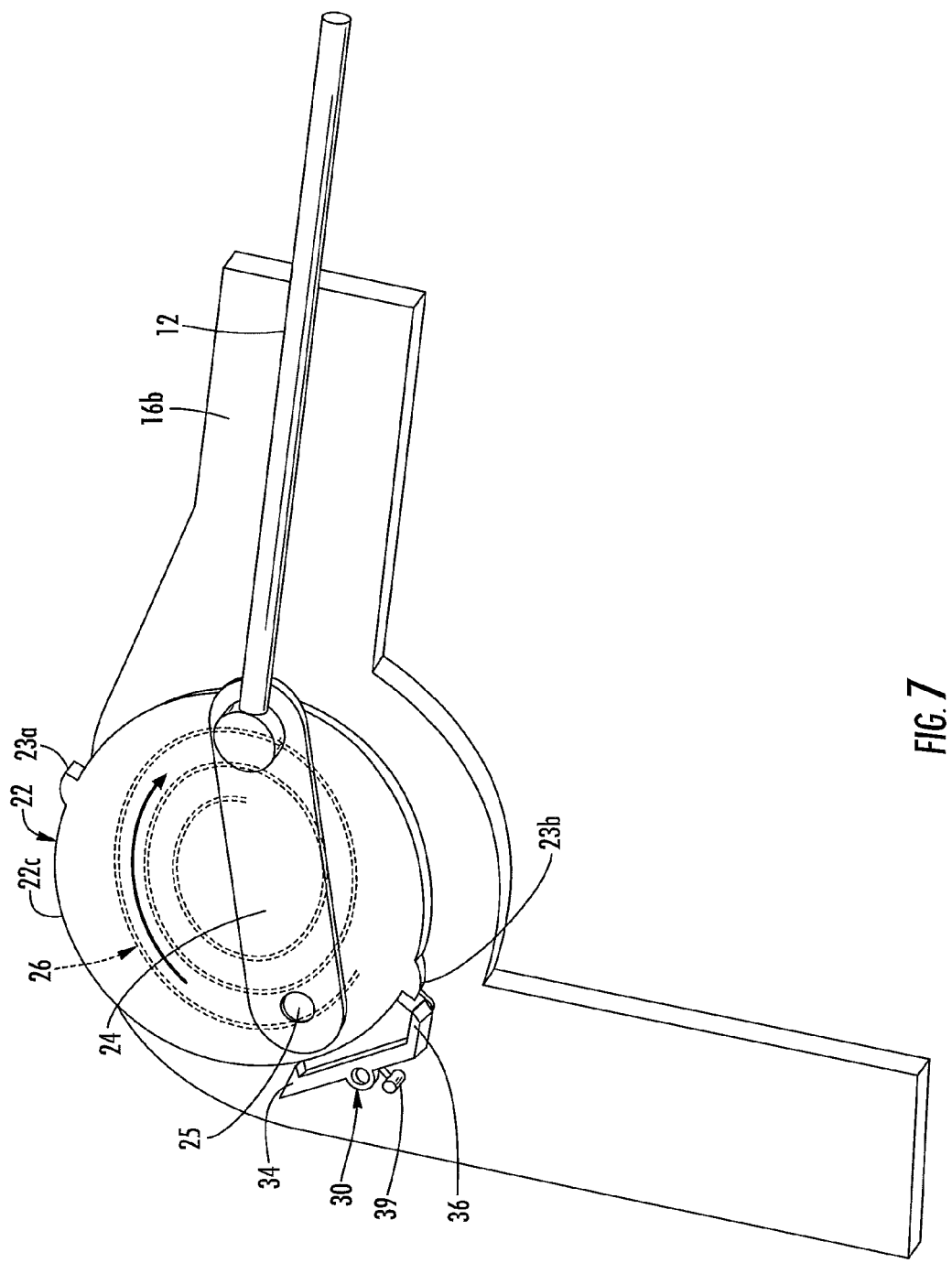

Referring to FIG. 7, release switch 32 is released such that release member 30 returns from the second condition to the first condition. In this embodiment, biasing member 39 returns release member 30 from the second condition to the first condition automatically. In this instance, stop 23*b* bypasses second catch 36 and rotates until stop 23*b* engages leading surface 34*a* of first catch 34 to complete the retraction of actuating rod 22. When stop 23*b* engages leading surface 34*a* of first catch 34, actuating rod 12 is held at its proximal-most position (see FIG. 8). As can be appreciated, when stops 23*a*, 23*b* are equally spaced on outer periphery 22*c* of rotating member 22, each engagement of release switch 32 permits rotating member 22 to rotate about 180° corresponding to a single retraction or extension of the actuating rod 12. It is contemplated that the 180° rotation of rotating member 22 corresponding to a retraction and/or an extension of actuation rod 12 occurs in about 0.2 seconds. However, deployment mechanism 20 can be configured to retract or extend actuation rod 12 in a quicker or slower manner via suitable mechanical augmenters or inhibitors, such as gears, damping fluids, pneumatics, hydraulics, etc.

Figure 8:
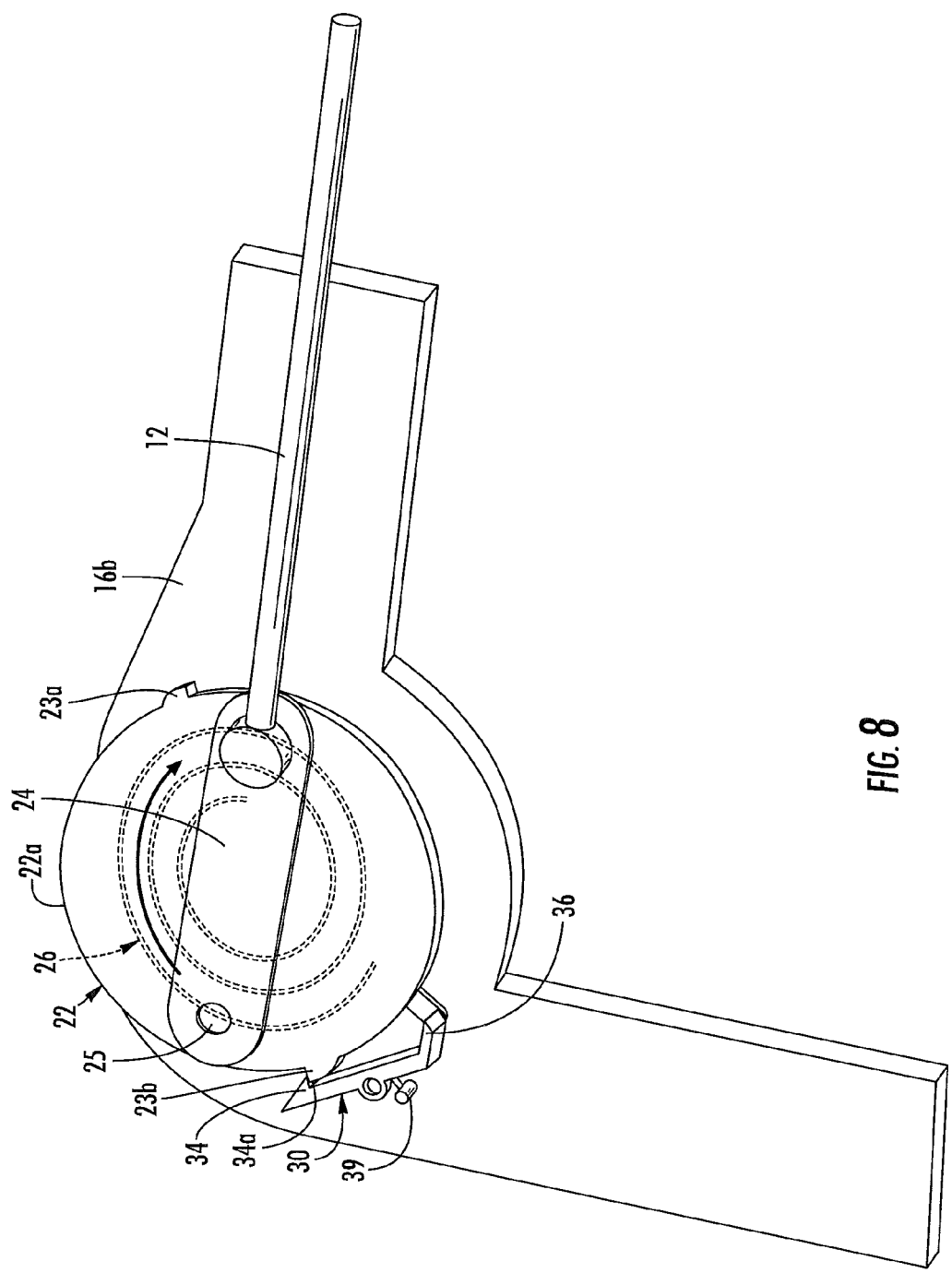

As shown in FIG. 8, to extend actuating rod 12, release switch 32 is again actuated to release stop 23*b* from catch 34 to permit further clockwise rotation of rotating member 22 until stop 23*a* engages second latch 36 (in the case of no biasing member 39) or stop 34 (in the case of biasing member 39 returning release member 30 to the first condition (see FIG. 4)).

Rotating member 22 may alternatively include a single stop such that each engagement of release switch 32 permits a full rotation or cycle of rotating member 22 corresponding to a retraction and an extension of actuating rod 12.

Deployment mechanism 20 may include more than one energy storage device (e.g., more than one spring), to increase the total amount of potential energy stored and allow more iterations of extension and retraction of the actuation rod 12. This increase in potential energy may increase the amount of energy or force released with each engagement of the release switch 32 and may increase the amount of force associated with each extension or retraction.

Other transmissions are also contemplated to convert the rotational energy of rotating member 22 to longitudinal translation of actuating rod 12 in place of connecting link 24 or cam 25. For example, one or more gear trains (not shown) may convert the rotation of rotating member 22 to translation of actuating rod 12.

Referring to FIG. 9, a crank arm 40 is used to wind energy storage device 26 (FIG. 2). Other mechanisms may be employed for this purpose and may include any suitable mechanical or electro-mechanical parts to facilitate winding of the energy storage device 26. As shown in FIGS. 1, 2, and 9, crank arm 40 engages a recess 29 (FIG. 1) in rotatable shaft 28 to rotate rotatable shaft 28 in a first direction (in this instance clockwise) to bias energy storage device 26 (FIG. 2), to generate potential energy in energy storage device 26. Rotatable shaft 28 is coupled to rotating member 22 (FIG. 2) such that rotating member 22 cooperates with the rotation of crank atm 40. Various gears and the like may be utilized to facilitate this process. Trailing surfaces 34b, 36b (FIG. 3) of first and second catches 34, 36 of release member 30 are angled such that as stops 23a, 23b (FIG. 4) engage trailing surfaces 34b, 36b, stops 23a, 23b urge catches 34, 36 away from outer peripheral edge 22c of rotating member 22 to permit unrestricted rotation of rotating member 22 when winding. Trailing surfaces 23t (see FIG. 4) of stops 23a, 23b may include a ramp (or the like) configured to cooperate with the angle of trailing surfaces 34b, 36b to facilitate winding of energy storage device 26. In some embodiments, release switch 32 may have an intermediate condition between the first and second positions such that both catches 34 and 36 are spaced-apart from peripheral edge 22c of rotating member such that stops 23a, 23b can pass between catches 34, 36 and peripheral edge 22c during the winding of energy storage device 26.

Other cranking mechanisms are also envisioned including but not limited to a recoil pull cord (not shown) that is wrapped around rotatable shaft 28 such that when the pull cord is pulled, the pull cord rotates rotatable shaft 28 to store energy within energy storage device 26. In such embodiments, rotatable shaft 28 includes a ratcheting mechanism (not shown) configured to permit rotating member 22 rotate in the first direction while rotatable shaft 28 remains stationary and configured to engage rotating member 22 such that rotating member 22 cooperates with rotation of rotatable shaft 28 in the second direction.

It is also contemplated that similar deployment mechanisms may be incorporated within existing surgical instruments, such as surgical staplers or vessel sealers, and may be utilized to translate actuating rod 12 to accomplish other purposes, e.g., deploy a knife, deploy staples, actuate jaw members from a first position spaced from one another to a second position for grasping tissue under a predetermined pressure for sealing tissue. For example and with particular respect to surgical staplers, rotating member 22 of deployment mechanism 20 can include stops 23a, 23b, etc. positioned about peripheral edge 22c of the rotating member 22 with each stop representing a position of the actuating rod, e.g., a stop for an unclamped position, a stop for the clamped position, a stop for the fire position, and a stop for the advance position. A single rotation of rotating member 22 can advance the actuating rod 12 to move a drive shaft (not shown) from the unclamped position through the clamped, fire, and advance positions. Deployment mechanism 20 can also include a gear system (not shown) between rotating member 22 and energy storage device 26 (or other energy storage device) such that the multiple rotations of energy storage device 26 are converted to a single rotation of the rotating member 22.

In some embodiments, deployment mechanism 20 may be configured to assist the clinician with clamping of tissue, firing of the plurality of staples, and severing of the tissue. In such embodiments, deployment mechanism 20 may be configured to provide a supplemental force to a mechanical deployment mechanism (e.g., handle) to assist with any of these functions.

In some embodiments, the instrument includes more than one actuation rod (not shown), a first actuation rod configured to clamp the tissue, a second actuation rod configured to fire the staples, and a third actuation rod configured to sever the tissue. In this instance, multiple cams 25 and links 24 may be utilized to accomplish the various purposes of the instrument.

In some embodiments, energy storage device 26 may be replaced or subsidized with a different or second energy storage device (not shown) that is configured to store electrical energy. In such embodiments, rotating shaft 28 is coupled to a generator (not shown) which is, in turn, electrically coupled to the alternate or second energy storage device. A separate actuator (not shown) may be included which is configured to release the energy from the alternate or second energy storage device to perform a second surgical function in addition to or in conjunction with sealing, cutting, cauterizing, coagulating, desiccating, and/or fulgurating tissue with RF energy. The energy storage device may be electrically coupled to a drive motor (not shown) that rotates one or more actuating rods 12 (or additional drive shaft(s) (not shown)) operatively associated with an end effector or the like.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:
1. A surgical instrument, comprising:
   a handle assembly having an actuating rod extending therefrom, the actuating rod defining a longitudinal axis therethrough and configured to translate therealong;
   a rotating member disposed within the handle assembly and operably engaged to the actuating rod via a cam and link arrangement that converts rotational movement of the rotating member into longitudinal translation of the actuating rod, the rotating member moveable in a first direction to bias an energy storage device;
   a release member including a first catch configured to lock the rotating member against the force of the energy storage device in a first condition and configured to release the rotating member to rotate in an opposite direction with the force of the energy storage device in a second condition; and
   at least one stop disposed on a peripheral edge of the rotating member, the at least one stop configured to operably engage the first catch when the release member is disposed in the first condition and configured to limit the rotational movement of the rotating member as the rotating member moves in the opposite direction, wherein the handle assembly includes a window and the energy storage device includes a power indicator, the power indicator viewable through the window.

2. The instrument of claim 1 further including a release switch configured to move the release member between the first and second conditions.

3. The instrument of claim 1, wherein the energy storage device is a torsion spring.

4. The instrument of claim 1, wherein the handle assembly includes an energy gauge proximate the window, the energy gauge cooperating with the power indicator to indicate an amount of energy stored by the energy storage device.

5. The instrument of claim 1 further including a release biasing member that urges the release member towards the first condition to limit rotational movement of the rotating member.

6. The instrument of claim 1, wherein the release member further includes a second catch that is selectively engagable with the at least one stop and configured to toggle with the first catch to limit the rotational movement of the rotating member.

7. The instrument of claim 1, wherein the at least one stop on a peripheral edge of the rotating member includes a first stop and a second stop equally spaced about the peripheral edge of rotating member relative to each other.

8. The instrument of claim 7, wherein the first stop is positioned on the peripheral edge of the rotating member such that when the first stop engages the first catch the actuating rod is disposed in an extended position and the second stop is positioned on the peripheral edge of the rotating member such that when the second stop engages the first catch the actuating rod is disposed in a retracted position.

9. The instrument of claim 1, wherein the actuating assembly includes a rotatable shaft operatively associated with the energy storage device, the rotatable shaft selectively moveable to rotate the rotating member against the bias of the energy storage device.

10. The instrument of claim 9 further including a crank configured to engage the rotatable shaft to manually rotate the rotating member to bias the energy storage device.

11. The instrument of claim 1, wherein the at least one stop includes a trailing surface having a ramp configured to urge the first catch of the release member away from the peripheral edge of the rotating member when the rotating member is rotated in the first direction to facilitate rotation of the rotating member to bias the energy storage device.

12. A method for actuating a surgical instrument, the method comprising:
  biasing an energy storage device of a surgical instrument in a first direction, the surgical instrument including:
    a handle assembly having an actuating rod extending therefrom, the actuating rod defining a longitudinal axis;
    a rotating member disposed within the handle assembly;
    a release member including a first catch; and
    at least one stop disposed on a peripheral edge of the rotating member;
  locking the rotating member against the force of the energy storage device by engaging the at least one stop with the first catch of the release member;
  translating the actuating rod along the longitudinal axis by releasing at least a portion of the energy from the energy storage device; and
  determining the amount of energy stored within the energy storage device by viewing a power indicator through a window defined by the handle assembly.

13. The method of claim 12, wherein translating the actuating rod includes converting the rotational movement of the rotating member into longitudinal translation of the actuating rod via a cam and link arrangement that operatively engages the rotating member and the actuating rod.

14. The method of claim 12, wherein biasing the energy storage device in a first direction includes the at least one stop urging the first catch of the release member away from the rotating member as the rotating member is rotated in the first direction.

15. The method of claim 12, wherein translating the actuating rod includes releasing the rotating member by disengaging the first catch of the release member from the at least one stop to permit the rotating member to rotate in a second direction opposite the first direction with the force of the energy storage device.

16. The method of claim 15 further including limiting the rotational movement of the rotating member as the rotating member moves in the second direction with a second catch of the release member.

17. The method of claim 15, wherein disengaging the first catch of the release member includes toggling a release switch operatively associated with the release member.

18. A surgical instrument, comprising:
  a handle assembly having an actuating rod extending therefrom, the actuating rod defining a longitudinal axis therethrough and configured to translate therealong;
  a rotating member disposed within the handle assembly and operably engaged to the actuating rod via a cam and link arrangement that converts rotational movement of the rotating member into longitudinal translation of the actuating rod, the rotating member moveable in a first direction to bias an energy storage device;
  a release member including a first catch configured to lock the rotating member against the force of the energy storage device in a first condition and configured to release the rotating member to rotate in an opposite direction with the force of the energy storage device in a second condition; and
  at least one stop disposed on a peripheral edge of the rotating member, the at least one stop configured to operably engage the first catch when the release member is disposed in the first condition and configured to limit the rotational movement of the rotating member as the rotating member moves in the opposite direction, wherein the release member further includes a second catch that is selectively engagable with the at least one stop and configured to toggle with the first catch to limit the rotational movement of the rotating member.

19. A surgical instrument, comprising:
  a handle assembly having an actuating rod extending therefrom, the actuating rod defining a longitudinal axis therethrough and configured to translate therealong;
  a rotating member disposed within the handle assembly and operably engaged to the actuating rod via a cam and link arrangement that converts rotational movement of the rotating member into longitudinal translation of the actuating rod, the rotating member moveable in a first direction to bias an energy storage device;
  a release member including a first catch configured to lock the rotating member against the force of the energy storage device in a first condition and configured to release the rotating member to rotate in an opposite direction with the force of the energy storage device in a second condition; and a pair of stops disposed on a peripheral edge of the rotating member, at least one of the plurality of stops configured to operably engage the first catch when the release member is disposed in the first condition and configured to limit the rotational movement of the rotating member as the rotating member moves in the opposite direction, the pair of stops equally spaced relative to one another about the peripheral edge of the rotating member, and wherein a first stop of the pair of stops is positioned on the peripheral edge of the rotating member such that when the first stop engages the first catch the actuating rod is disposed in an extended position and wherein a second stop of the pair of stops is positioned on the peripheral edge of the rotating member such that when the second stop engages the first catch the actuating rod is disposed in a retracted position.

20. A method for actuating a surgical instrument, the method comprising:

biasing an energy storage device of a surgical instrument in a first direction, the surgical instrument including:

a handle assembly having an actuating rod extending therefrom, the actuating rod defining a longitudinal axis;

a rotating member disposed within the handle assembly;

a release member including a first catch; and at least one stop disposed on a peripheral edge of the rotating member;

locking the rotating member against the force of the energy storage device by engaging the at least one stop with the first catch of the release member; and translating the actuating rod along the longitudinal axis by releasing at least a portion of the energy from the energy storage device wherein translating the actuating rod includes releasing the rotating member by disengaging the first catch of the release member from the at least one stop to permit the rotating member to rotate in a second direction opposite the first direction with the force of the energy storage device; and limiting the rotational movement of the rotating member as the rotating member moves in the second direction with a second catch of the release member.

21. A method for actuating a surgical instrument, the method comprising:

biasing an energy storage device of a surgical instrument in a first direction, the surgical instrument including:

a handle assembly having an actuating rod extending therefrom, the actuating rod defining a longitudinal axis;

a rotating member disposed within the handle assembly;

a release member including a first catch; and at least one stop disposed on a peripheral edge of the rotating member;

locking the rotating member against the force of the energy storage device by engaging the at least one stop with the first catch of the release member; and translating the actuating rod along the longitudinal axis by releasing at least a portion of the energy from the energy storage device wherein biasing the energy storage device in a first direction includes the at least one stop urging the first catch of the release member away from the rotating member as the rotating member is rotated in the first direction.

* * * * *